United States Patent [19]

DeFeo-Jones et al.

[11] Patent Number: 5,599,686
[45] Date of Patent: Feb. 4, 1997

[54] PEPTIDES

[75] Inventors: Deborah DeFeo-Jones, Lansdale; Victor M. Garsky, Blue Bell; Raymond E. Jones, Lansdale; Allen I. Oliff, Gwynedd Valley, all of Pa.

[73] Assignee: Merck & Co., Inc., Rahway, N.J.

[21] Appl. No.: 267,092

[22] Filed: Jun. 28, 1994

[51] Int. Cl.$^6$ .............................. C12Q 1/37; C12Q 1/34; A61K 38/14

[52] U.S. Cl. .................... 435/23; 435/24; 435/18; 435/7.23; 435/7.1; 435/4; 424/185.1; 530/322; 530/300

[58] Field of Search .................... 435/8, 23, 24, 435/18, 7.23, 7.1, 4, 2; 424/185.1; 530/322, 300

[56] References Cited

U.S. PATENT DOCUMENTS

| | | | |
|---|---|---|---|
| 4,277,466 | 7/1981 | Trouet | 424/185.1 |
| 4,296,105 | 10/1981 | Baurain et al. | 424/185.1 |
| 4,388,305 | 6/1983 | Trouet et al. | 424/185.1 |
| 4,446,122 | 5/1984 | Chu et al. | 435/4 |
| 4,828,831 | 5/1989 | Hannart et al. | 424/185.1 |
| 5,024,835 | 6/1991 | Rao et al. | 424/185.1 |
| 5,030,620 | 7/1991 | Hannart et al. | 514/8 |
| 5,116,615 | 5/1992 | Gokeen et al. | 435/8 |
| 5,227,471 | 7/1993 | Wright, Jr. | 435/8 |
| 5,288,612 | 2/1994 | Griffin et al. | 435/23 |
| 5,314,996 | 5/1994 | Wright, Jr. | 435/8 |
| 5,332,669 | 7/1994 | Devel | 435/8 |
| 5,349,066 | 9/1994 | Kaneko et al. | 546/294 |
| 5,391,723 | 2/1995 | Priest | 536/23.1 |

FOREIGN PATENT DOCUMENTS

| | | |
|---|---|---|
| 0554708A1 | 8/1993 | European Pat. Off. . |
| 0590530A2 | 4/1994 | European Pat. Off. . |
| 2678274A1 | 12/1992 | France . |
| 92/01936 | 2/1992 | WIPO . |
| WO94/10343 | 5/1994 | WIPO . |
| 94/20114 | 9/1994 | WIPO . |
| WO95/30758 | 11/1995 | WIPO . |

OTHER PUBLICATIONS

Trail, P. A. et al., Cure of Xenografted Human Carcinomas by BR96–Doxorubicin Immunoconjugates, Science, vol. 261, pp. 212–215 (1993).

Willner, D. et al., (6–Maleimidocaproyl)hydrazone of Doxorubicin—A New Derivative for the Preparation of Immunoconjugates of Doxorubicin, Bioconjugate Chem., vol. 4, pp. 521–527 (1993).

Yu, H. et al., Immunoreactive Prostate–Specific Antigen Levels in Female and Male Breast Tumors and its Association with Steroid Hormone Receptors and Patient Age, Clinical Biochemistry, vol. 27, pp. 75–79 (1994).

Lilja, H. and Lundwall, A., "Molecular cloning of epididymal and seminal vesicular transcripts encoding a semenogelin–related protein," Proc. Natl. Acad, Sci. USA, Biochemistry, vol. 89, pp. 4559–4563 (1992).

Lilja, H., et al., "Semenogelin, the Predominant Protein in Human Semen," The Jour. of Biol. Chem., vol. 264, No. 3, pp. 1894–1900 (1989).

Christensson et al, "Eur. J. Biochem", vol. 194, pp. 755–763, 1990.

Watt et al, "Proc. Natl. Acad. Sci.", vol. 83, pp. 3166–3170, 1986.

*Primary Examiner*—Ralph Gitomer
*Assistant Examiner*—Louise Leary
*Attorney, Agent, or Firm*—David A. Muthard; Mark R. Daniel

[57] ABSTRACT

Assays which comprise oligopeptides and which are useful for determining free PSA protease activity in vitro and in vivo are described. Such oligopeptides comprise amino acid sequences that are recognized and proteolytically cleaved by free prostrate specific antigen (PSA). Also described are assays useful in identifying inhibitors of free PSA.

15 Claims, 4 Drawing Sheets

1:    MetLysProAsnIleIlePheValLeuSerLeuLeuLeuIleLeuGluLysGlnAlaAla -

21:   ValMetGlyGlnLysGlyGlySerLysGlyArgLeuProSerGluPheSerGlnPhePro -

41:   HisGlyGlnLysGlyGlnHisTyrSerGlyGlnLysGlyLysGlnGlnThrGluSerLys -

61:   GlySerPheSerIleGlnTyrThrTyrHisValAspAlaAsnAspHisAspGlnSerArg -

81:   LysSerGlnGlnTyrAspLeuAsnAlaLeuHisLysThrThrLysSerGlnArgHisLeu -

101:  GlyGlySerGlnGlnLeuLeuHisAsnLysGlnGluGlyArgAspHisAspLysSerLys -

121:  GlyHisPheHisArgValValIleHisHisLysGlyGlyLysAlaHisArgGlyThrGln -

CS#5
141:  AsnProSerGlnAspGlnGlyAsnSerProSerGlyLysGlyIleSerSerGlnTyr|Ser -

161:  AsnThrGluGluArgLeuTrpValHisGlyLeuSerLysGluGlnThrSerValSerGly -

181:  AlaGlnLysGlyArgLysGlnGlyGlySerGlnSerSerTyrValLeuGlnThrGluGlu -

201:  LeuValAlaAsnLysGlnGlnArgGluThrLysAsnSerHisGlnAsnLysGlyHisTyr -

221:  GlnAsnValValGluValArgGluGluHisSerSerLysValGlnThrSerLeuCysPro -

241:  AlaHisGlnAspLysLeuGlnHisGlySerLysAspIlePheSerThrGlnAspGluLeu -

FIG.1A

261: LeuValTyrAsnLysAsnGlnHisGlnThrLysAsnLeuAsnGlnAspGlnGlnHisGly -

CS#3
281: ArgLysAlaAsnLysIleSerTyrGln|SerSerSerThrGluGluArgArgLeuHisTyr -

CS#4
301: GlyGluAsnGlyValGlnLysAspValSerGlnSerSerIleTyrSer|GlnThrGluGlu -

321: LysAlaGlnGlyLysSerGlnLysGlnIleThrIleProSerGlnGluGlnGluHisSer -

CS#1
341: GlnLysAlaAsnLysIleSerTyrGln|SerSerSerThrGluGluArgArgLeuHisTyr -

CS#2
361: GlyGluAsnGlyValGlnLysAspValSerGlnArgSerIleTyrSer|GlnThrGluLys -

381: LeuValAlaGlyLysSerGlnIleGlnAlaProAsnProLysGlnGluProTrpHisGly -

401: GluAsnAlaLysGlyGluSerGlyGlnSerThrAsnArgGluGlnAspLeuLeuSerHis -

421: GluGlnLysGlyArgHisGlnHisGlySerHisGlyGlyLeuAspIleValIleIleGlu -

441: GlnGluAspAspSerAspArgHisLeuAlaGlnHisLeuAsnAsnAspArgAsnProLeu -

461: PheThr -

FIG.1B

PERCENT PEPTIDE HYDROLYSIS

| PEPTIDE | TIME OF INCUBATION (HOURS) | | | | | |
|---|---|---|---|---|---|---|
| | 0.5 | 1 | 2 | 3 | 4 | 20 |
| 1. SYQSSSTE | ND | 0 | ND | 0 | ND | 0 |
| 2. ISYQSSSTE | ND | 0 | ND | 0 | ND | 0 |
| 3. KISYQSSSTE | ND | 10 | ND | 30 | ND | 90 |
| 4. NKISYQSSSTE | ND | 30 | ND | 70 | ND | 100 |
| 5. NKISYQSSST | ND | 20 | 30 | ND | ND | 100 |
| 6. ANKISYQSSSTE | 15 | 25 | ND | ND | 80 | 100 |
| 7. ANKISYQSSS | 4 | 6 | 16 | 30 | 45 | ND |
| 8. NKISYQSSS | 2 | 6 | 22 | 44 | 55 | ND |
| 9. ANKISYQSS | 1 | ND | 12 | ND | 39 | ND |
| 10. GRKANKISYQS-SSTEERRLHYGENG | 20 | 50 | ND | ND | 90 | 100 |

ND = NOT DETERMINED

FIG. 2

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
( A ) LENGTH: 462 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

| Met | Lys | Pro | Asn | Ile | Ile | Phe | Val | Leu | Ser | Leu | Leu | Leu | Ile | Leu | Glu |
|---|---|---|---|---|---|---|---|---|---|---|---|---|---|---|---|
| 1 | | | | 5 | | | | | 10 | | | | | 15 | |
| Lys | Gln | Ala | Ala | Val | Met | Gly | Gln | Lys | Gly | Gly | Ser | Lys | Gly | Arg | Leu |
| | | | 20 | | | | | 25 | | | | | 30 | | |
| Pro | Ser | Glu | Phe | Ser | Gln | Phe | Pro | His | Gly | Gln | Lys | Gly | Gln | His | Tyr |
| | | 35 | | | | | 40 | | | | | 45 | | | |
| Ser | Gly | Gln | Lys | Gly | Lys | Gln | Gln | Thr | Glu | Ser | Lys | Gly | Ser | Phe | Ser |
| | 50 | | | | | 55 | | | | | 60 | | | | |
| Ile | Gln | Tyr | Thr | Tyr | His | Val | Asp | Ala | Asn | Asp | His | Asp | Gln | Ser | Arg |
| 65 | | | | | 70 | | | | | 75 | | | | | 80 |
| Lys | Ser | Gln | Gln | Tyr | Asp | Leu | Asn | Ala | Leu | His | Lys | Thr | Thr | Lys | Ser |
| | | | | 85 | | | | | 90 | | | | | 95 | |
| Gln | Arg | His | Leu | Gly | Gly | Ser | Gln | Gln | Leu | Leu | His | Asn | Lys | Gln | Glu |
| | | | | 100 | | | | | 105 | | | | | 110 | |
| Gly | Arg | Asp | His | Asp | Lys | Ser | Lys | Gly | His | Phe | His | Arg | Val | Val | Ile |
| | | 115 | | | | | 120 | | | | | 125 | | | |
| His | His | Lys | Gly | Gly | Lys | Ala | His | Arg | Gly | Thr | Gln | Asn | Pro | Ser | Gln |
| | 130 | | | | | 135 | | | | | 140 | | | | |
| Asp | Gln | Gly | Asn | Ser | Pro | Ser | Gly | Lys | Gly | Ile | Ser | Ser | Gln | Tyr | Ser |
| 145 | | | | | 150 | | | | | 155 | | | | | 160 |
| Asn | Thr | Glu | Glu | Arg | Leu | Trp | Val | His | Gly | Leu | Ser | Lys | Glu | Gln | Thr |
| | | | | 165 | | | | | 170 | | | | | 175 | |
| Ser | Val | Ser | Gly | Ala | Gln | Lys | Gly | Arg | Lys | Gln | Gly | Gly | Ser | Gln | Ser |
| | | | 180 | | | | | 185 | | | | | 190 | | |
| Ser | Tyr | Val | Leu | Gln | Thr | Glu | Glu | Leu | Val | Ala | Asn | Lys | Gln | Gln | Arg |
| | | 195 | | | | | 200 | | | | | 205 | | | |
| Glu | Thr | Lys | Asn | Ser | His | Gln | Asn | Lys | Gly | His | Tyr | Gln | Asn | Val | Val |
| | 210 | | | | | 215 | | | | | 220 | | | | |
| Glu | Val | Arg | Glu | Glu | His | Ser | Ser | Lys | Val | Gln | Thr | Ser | Leu | Cys | Pro |
| 225 | | | | | 230 | | | | | 235 | | | | | 240 |
| Ala | His | Gln | Asp | Lys | Leu | Gln | His | Gly | Ser | Lys | Asp | Ile | Phe | Ser | Thr |
| | | | | 245 | | | | | 250 | | | | | 255 | |
| Gln | Asp | Glu | Leu | Leu | Val | Tyr | Asn | Lys | Asn | Gln | His | Gln | Thr | Lys | Asn |
| | | | 260 | | | | | 265 | | | | | 270 | | |
| Leu | Asn | Gln | Asp | Gln | Gln | His | Gly | Arg | Lys | Ala | Asn | Lys | Ile | Ser | Tyr |
| | | 275 | | | | | 280 | | | | | 285 | | | |

```
         Gln  Ser  Ser  Ser  Thr  Glu  Glu  Arg  Arg  Leu  His  Tyr  Gly  Glu  Asn  Gly
              290                 295                      300

Val  Gln  Lys  Asp  Val  Ser  Gln  Ser  Ser  Ile  Tyr  Ser  Gln  Thr  Glu  Glu
         305                      310                      315                      320

Lys  Ala  Gln  Gly  Lys  Ser  Gln  Lys  Gln  Ile  Thr  Ile  Pro  Ser  Gln  Glu
                             325                      330                      335

Gln  Glu  His  Ser  Gln  Lys  Ala  Asn  Lys  Ile  Ser  Tyr  Gln  Ser  Ser  Ser
                        340                      345                      350

Thr  Glu  Glu  Arg  Arg  Leu  His  Tyr  Gly  Glu  Asn  Gly  Val  Gln  Lys  Asp
                   355                      360                      365

Val  Ser  Gln  Arg  Ser  Ile  Tyr  Ser  Gln  Thr  Glu  Lys  Leu  Val  Ala  Gly
              370                      375                      380

Lys  Ser  Gln  Ile  Gln  Ala  Pro  Asn  Pro  Lys  Gln  Glu  Pro  Trp  His  Gly
         385                      390                      395                      400

Glu  Asn  Ala  Lys  Gly  Glu  Ser  Gly  Gln  Ser  Thr  Asn  Arg  Glu  Gln  Asp
                             405                      410                      415

Leu  Leu  Ser  His  Glu  Gln  Lys  Gly  Arg  His  Gln  His  Gly  Ser  His  Gly
                        420                      425                      430

Gly  Leu  Asp  Ile  Val  Ile  Ile  Glu  Gln  Glu  Asp  Asp  Ser  Asp  Arg  His
                        435                      440                      445

Leu  Ala  Gln  His  Leu  Asn  Asn  Asp  Arg  Asn  Pro  Leu  Phe  Thr
              450                      455                      460
```

( 2 ) INFORMATION FOR SEQ ID NO:2:

( i ) SEQUENCE CHARACTERISTICS:
       ( A ) LENGTH: 15 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
         Gly  Lys  Gly  Ile  Ser  Ser  Gln  Tyr  Ser  Asn  Thr  Glu  Glu  Arg  Leu
         1                 5                      10                          15
```

( 2 ) INFORMATION FOR SEQ ID NO:3:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
         Asn  Lys  Ile  Ser  Tyr  Gln  Ser  Ser  Ser  Thr  Glu
         1                 5                      10
```

( 2 ) INFORMATION FOR SEQ ID NO:4:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

```
Gly Glu Asn Gly Val Gln Lys Asp Val Ser Gln Arg Ser Ile Tyr Ser
 1               5                  10                  15
Gln Thr Glu
```

( 2 ) INFORMATION FOR SEQ ID NO:5:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

```
Gly Glu Asn Gly Val Gln Lys Asp Val Ser Gln Ser Ser Ile Tyr Ser
 1               5                  10                  15
Gln Thr Glu
```

( 2 ) INFORMATION FOR SEQ ID NO:6:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Gly Arg Lys Ala Asn Lys Ile Ser Tyr Gln Ser Ser Ser Thr Glu Glu
 1               5                  10                  15
Arg Arg Leu His Tyr Gly Glu Asn Gly
                 20                  25
```

( 2 ) INFORMATION FOR SEQ ID NO:7:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

Ser Tyr Gln Ser Ser Ser Thr Glu
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v.) FRAGMENT TYPE: internal ( x i ) SEQUENCE DESCRIPTION: SEQ ID NO:8:

Ile Ser Tyr Gln Ser Ser Ser Thr Glu
1                   5

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

Lys Ile Ser Tyr Gln Ser Ser Ser Thr Glu
1                   5                   10

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

Asn Lys Ile Ser Tyr Gln Ser Ser Ser Thr
1                   5                   10

( 2 ) INFORMATION FOR SEQ ID NO:11:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

```
Ala  Asn  Lys  Ile  Ser  Tyr  Gln  Ser  Ser  Ser  Thr  Glu
 1                    5                         10
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

```
Ala  Ser  Ala  Gly  Thr  Pro  Gly  Ala
 1                    5
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

```
Asn  Lys  Ile  Ser  Tyr  Gln  Ser
 1                    5
```

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal ( x i ) SEQUENCE DESCRIPTION: SEQ ID NO:14:

Lys Ile Ser Tyr Gln Ser
1               5

( 2 ) INFORMATION FOR SEQ ID NO:15:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

Gly Glu Asn Gly Val Gln Lys Asp Val Xaa Gln Xaa Ser Ile Tyr Ser
1               5                   10                  15
Gln Thr Glu ( 2 ) INFORMATION FOR SEQ ID NO:16:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

Asn Lys Ile Ser Tyr Gln Ser Ser
1               5

( 2 ) INFORMATION FOR SEQ ID NO:17:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

Asn Lys Ile Ser Tyr Gln Ser Ser Ser
1               5

( 2 ) INFORMATION FOR SEQ ID NO:18:

( i ) SEQUENCE CHARACTERISTICS:
( A ) LENGTH: 10 amino acids
( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

```
Ala  Asn  Lys  Ile  Ser  Tyr  Gln  Ser  Ser  Ser
1                 5                      10
```

(2) INFORMATION FOR SEQ ID NO:19:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

```
Lys  Ile  Ser  Tyr  Gln  Ser  Ser  Ser  Thr  Glu
1                 5                      10
```

(2) INFORMATION FOR SEQ ID NO:20:

(i) SEQUENCE CHARACTERISTICS:
  (A) LENGTH: 17 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

```
Gln  Leu  Asp  Asn  Lys  Ile  Ser  Tyr  Gln  Ser  Ser  Ser  Thr  His  Gln  Ser
1                 5                      10                       15
Ser
```

(2) INFORMATION FOR SEQ ID NO:21:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:21:

```
Asn  Arg  Ile  Ser  Tyr  Gln  Ser
1                   5
```

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

```
Asn  Lys  Val  Ser  Tyr  Gln  Ser
1                   5
```

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:23:

```
Asn  Lys  Met  Ser  Tyr  Gln  Ser  Ser
1                   5
```

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:24:

```
Asn  Lys  Leu  Ser  Tyr  Gln  Ser  Ser
1                   5
```

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:25:

Asn Lys Ile Thr Tyr Gln Ser Ser Ser
1               5

( 2 ) INFORMATION FOR SEQ ID NO:26:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:26:

Asn Lys Ile Ser Phe Gln Ser Ser Ser
1               5

( 2 ) INFORMATION FOR SEQ ID NO:27:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:27:

Asn Lys Ile Ser Trp Gln Ser Ser Ser Thr
1               5                   10

( 2 ) INFORMATION FOR SEQ ID NO:28:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:28:

Asn Lys Ile Ser Tyr Asn Ser Ser Ser Thr
1               5                   10

( 2 ) INFORMATION FOR SEQ ID NO:29:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:29:

Asn Lys Ile Ser Tyr Gln Thr Ser Ser Thr
1               5                   10

(2) INFORMATION FOR SEQ ID NO:30:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:30:

Asn Lys Ile Ser Tyr Gln Ser
1               5

(2) INFORMATION FOR SEQ ID NO:31:

(i) SEQUENCE CHARACTERISTICS:
  (A) LENGTH: 8 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:31:

Gln Lys Ile Ser Tyr Gln Ser Ser
1               5

(2) INFORMATION FOR SEQ ID NO:32:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal ( x i ) SEQUENCE DESCRIPTION: SEQ ID NO:32:

Asn Arg Ile Thr Tyr Gln Ser Ser Ser
1               5

( 2 ) INFORMATION FOR SEQ ID NO:33:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:33:

Asn Arg Ile Ser Phe Gln Ser Ser Ser Thr
1               5                   1 0

( 2 ) INFORMATION FOR SEQ ID NO:34:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:34:

Asn Arg Ile Ser Trp Gln Ser Ser Ser Thr
1               5                   1 0

( 2 ) INFORMATION FOR SEQ ID NO:35:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:35:

Asn Arg Ile Ser Tyr Gln Thr Ser Ser Thr
1               5                   1 0

( 2 ) INFORMATION FOR SEQ ID NO:36:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:36:

```
Asn Lys Ile Thr Tyr Gln Thr Ser Ser Thr
1               5                   10
```

( 2 ) INFORMATION FOR SEQ ID NO:37:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:37:

```
Asn Lys Leu Ser Tyr Gln Thr Ser Ser Thr
1               5                   10
```

( 2 ) INFORMATION FOR SEQ ID NO:38:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:38:

```
Gln Lys Leu Ser Tyr Gln Ser Ser Ser Thr
1               5                   10
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:39:

```
Asn Arg Leu Ser Tyr Gln Thr Ser Ser Thr
1               5                   10
```

( 2 ) INFORMATION FOR SEQ ID NO:40:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:40:

```
Asn  Lys  Val  Ser  Phe  Gln  Ser  Ser  Ser  Thr
1                  5                       1 0
```

( 2 ) INFORMATION FOR SEQ ID NO:41:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:41:

```
Asn  Arg  Val  Ser  Trp  Gln  Ser  Ser  Ser  Thr
1                  5                       1 0
```

( 2 ) INFORMATION FOR SEQ ID NO:42:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:42:

```
Gln  Lys  Val  Ser  Tyr  Gln  Ser  Ser  Ser  Thr
1                  5                       1 0
```

( 2 ) INFORMATION FOR SEQ ID NO:43:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:43:

Asn Lys Ile Ser Tyr Gln Ser Ser Ser Thr
1               5                   10

( 2 ) INFORMATION FOR SEQ ID NO:44:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:44:

Asn Lys Ile Ser Tyr Gln Ser Ser Ser Thr
1               5                   10

( 2 ) INFORMATION FOR SEQ ID NO:45:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:45:

Gly Glu Gln Gly Val Gln Lys Asp Val Ser Gln Ser Ser Ile Tyr Ser
1               5                   10                  15

Gln Thr Glu ( 2 ) INFORMATION FOR SEQ ID NO:46:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:46:

Gly Glu Asn Gly Leu Gln Lys Asp Val Ser Gln Ser Ser Ile Tyr Ser
1               5                   10                  15

Gln Thr Glu ( 2 ) INFORMATION FOR SEQ ID NO:47:

(i) SEQUENCE CHARACTERISTICS:
 (A) LENGTH: 19 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:47:

Gly Glu Asn Gly Val Asn Lys Asp Val Ser Gln Ser Ser Ile Tyr Ser
1               5                   10                  15
Gln Thr Glu (2) INFORMATION FOR SEQ ID NO:48:

(i) SEQUENCE CHARACTERISTICS:
 (A) LENGTH: 19 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:48:

Gly Glu Asn Gly Val Gln Arg Asp Val Ser Gln Arg Ser Ile Tyr Ser
1               5                   10                  15
Gln Thr Glu (2) INFORMATION FOR SEQ ID NO:49:

(i) SEQUENCE CHARACTERISTICS:
 (A) LENGTH: 19 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:49:

Gly Glu Asn Gly Val Gln Lys Asp Val Ser Gln Lys Ser Ile Tyr Ser
1               5                   10                  15
Gln Thr Glu (2) INFORMATION FOR SEQ ID NO:50:

(i) SEQUENCE CHARACTERISTICS:
 (A) LENGTH: 19 amino acids
 (B) TYPE: amino acid
 (C) STRANDEDNESS: single
 (D) TOPOLOGY: linear (ii) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:50:

Gly Glu Asn Gly Val Gln Lys Asp Leu Ser Gln Thr Ser Ile Tyr Ser
1               5                   10                  15

Gln Thr Glu (2) INFORMATION FOR SEQ ID NO:51:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:51:

Gly Glu Asn Gly Val Gln Lys Asp Val Ser Gln Ser Ser Ile Phe Ser
1               5                   10                  15

Gln Thr Glu (2) INFORMATION FOR SEQ ID NO:52:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:52:

Gly Glu Asn Gly Val Gln Lys Asp Met Ser Gln Ser Ser Ile Tyr Thr
1               5                   10                  15

Gln Thr Glu (2) INFORMATION FOR SEQ ID NO:53:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:53:

```
      Gly  Glu  Asn  Gly  Val  Gln  Lys  Asp  Val  Ser  Gln  Arg  Ser  Ile  Tyr  Thr
      1              5                        10                       15

Gln  Thr  Glu
```

( 2 ) INFORMATION FOR SEQ ID NO:54:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:54:

```
      Gly  Glu  Asn  Gly  Val  Gln  Lys  Asp  Val  Ser  Gln  Ser  Ser  Ile  Tyr  Ser
      1              5                        10                       15

Gln  Ser  Glu
```

( 2 ) INFORMATION FOR SEQ ID NO:55:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:55:

```
      Gly  Glu  Asn  Gly  Val  Gln  Lys  Asp  Val  Ser  Gln  Arg  Ser  Ile  Tyr  Ser
      1              5                        10                       15

Asn  Thr  Glu
```

( 2 ) INFORMATION FOR SEQ ID NO:56:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:56:

```
      Gly  Lys  Ala  Ile  Ser  Ser  Gln  Tyr  Ser  Asn  Thr  Glu  Glu  Arg  Leu
      1              5                        10                       15
```

( 2 ) INFORMATION FOR SEQ ID NO:57:

( i ) SEQUENCE CHARACTERISTICS:

( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:57:

Gly Arg Gly Ile Ser Ser Gln Tyr Ser Asn Thr Glu Glu Arg Leu
1               5                   10                  15

( 2 ) INFORMATION FOR SEQ ID NO:58:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:58:

Gly Lys Gly Ile Thr Ser Gln Tyr Ser Asn Thr Glu Glu Arg Leu
1               5                   10                  15

( 2 ) INFORMATION FOR SEQ ID NO:59:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:59:

Gly Lys Gly Ile Ser Thr Gln Tyr Ser Asn Thr Glu Glu Arg Leu
1               5                   10                  15

( 2 ) INFORMATION FOR SEQ ID NO:60:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:60:

```
            Gly  Lys  Gly  Ile  Ser  Ser  Asn  Tyr  Ser  Asn  Thr  Glu  Glu  Arg  Leu
             1                  5                        10                       15
```

( 2 ) INFORMATION FOR SEQ ID NO:61:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:61:

```
            Ala  Lys  Gly  Ile  Ser  Ser  Gln  Tyr  Ser  Asn  Thr  Glu  Glu  Arg  Leu
             1                  5                        10                       15
```

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:62:

```
            Gly  Lys  Gly  Ile  Ser  Ser  Gln  Phe  Ser  Asn  Thr  Glu  Glu  Arg  Leu
             1                  5                        10                       15
```

( 2 ) INFORMATION FOR SEQ ID NO:63:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:63:

```
            Gly  Lys  Gly  Ile  Ser  Ser  Gln  Tyr  Thr  Asn  Thr  Glu  Glu  Arg  Leu
             1                  5                        10                       15
```

( 2 ) INFORMATION FOR SEQ ID NO:64:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:64:

Gly Lys Gly Ile Ser Ser Gln Tyr Ser Asn Ser Glu Glu Arg Leu
1               5                   10                  15

(2) INFORMATION FOR SEQ ID NO:65:

(i) SEQUENCE CHARACTERISTICS:
  (A) LENGTH: 15 amino acids
  (B) TYPE: amino acid
  (C) STRANDEDNESS: single
  (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:65:

Gly Lys Gly Ile Ser Ser Gln Tyr Ser Asn Thr Asp Glu Arg Leu
1               5                   10                  15

PEPTIDES

BACKGROUND OF THE INVENTION

In 1994 cancer of the prostate gland is expected to be diagnosed in 200,000 men in the U.S. and 38,000 American males will die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christensson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Björk, T., Nilsson, O., et al. (1993). J. Urol. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since them is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

Accordingly, it is the object of this invention to provide novel oligopeptides which selectively are enzymatically cleaved by active free prostate specific antigen (PSA).

It is also the object of this invention to provide a quantitative assay for enzymatically active PSA which incorporates those novel oligopeptides.

It is further the object of this invention to provide a novel anti-cancer composition useful for the treatment of prostate cancer which comprises those novel oligopeptides in conjugation with a cytotoxic agent.

Another object of this invention is to provide a method of treating prostate cancer which comprises administration of novel anti-cancer composition.

SUMMARY OF THE INVENTION

The several points of cleavage where semenogelin I is selectively proteolytically cleaved by free PSA have been identified. Oligopeptides which comprise the amino acid sequences that are recognized and proteolytically cleaved by free prostrate specific antigen (PSA) are described. Such oligopeptides are useful in assays which can determine the free PSA protease activity in vitro and in vivo. Furthermore, such oligopeptides may be incorporated into therapeutic agents which comprise conjugates of such oligopeptides and known cytotoxic agents and which are useful in the treatment of prostatic cancer.

BRIEF DESCRIPTION OF THE FIGURES

FIG. 1: Primary Amino Acid Sequence of Semenogelin I:

Figure 3:
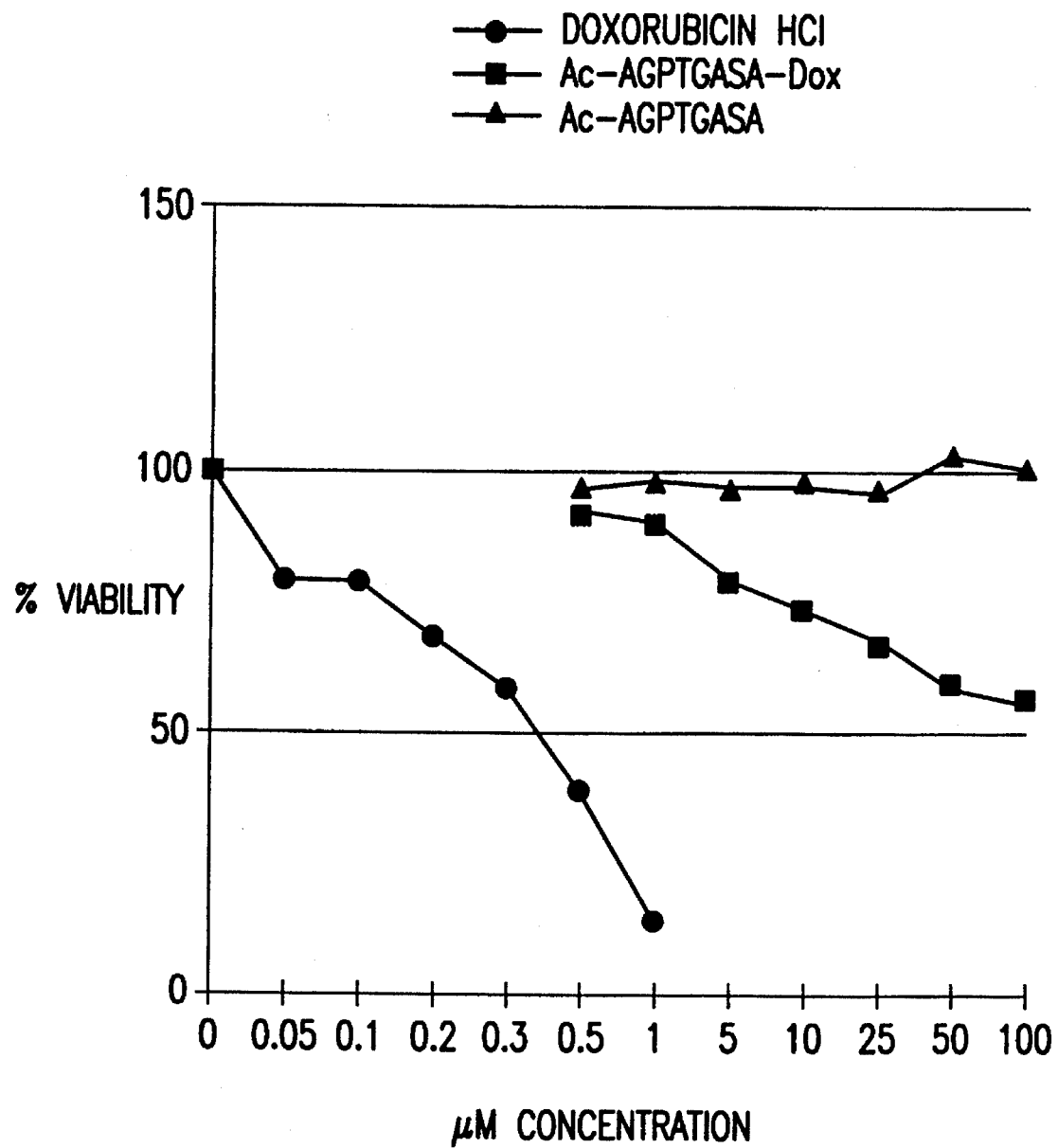

The primary amino acid sequence of Semenogelin I is shown. (SEQ.ID.NO.: 1) The PSA proteolytic cleavage sites ("CS") are shown (numbered in order of the relative affinity of a site towards PSA hydrolysis) and the protein fragments are numbered sequentially starting at the amino terminus.

FIG. 2: Cleavage Affinity of Synthetic Oligopeptides:

A nested set of synthetic oligopeptides was prepared and the oligopeptides were digested with enzymatically active free PSA for various times. The results are shown in Table 2.

FIG. 3: Cytotoxicity Data of Non-cleavable Oligopeptide-Doxorubicin Conjugates:

The data of the figure shows comparative cytotoxicity of doxorubicin and a conjugate of doxorubicin covalently bound to an oligopeptide (Compound 12d) that does not contain the free PSA proteolytic cleavage site. The $IC_{50}$ for doxorubicin is 0.3 µM, while the acetylated oligopeptide modified doxorubicin has an $IC_{50}$ that has been reduced by greater than 300 fold. This conjugate had no HPLC detectable contamination with unmodified doxorubicin. The oligopeptide alone had no detectable cell killing activity.

DETAILED DESCRIPTION OF THE INVENTION

The present invention relates to novel oligopeptides which are specifically recognized by the free prostate specific antigen (PSA) and are capable of being proteolytically cleaved by the enzymatic activity of the free prostate specific antigen. Such oligopeptides include oligomers that comprise an amino acid sequence selected from:

a) AsnLysIleSerTyrGln|Ser (SEQ.ID.NO.: 13), b) LysIleSerTyrGln|Ser (SEQ.ID.NO.: 14), c) GlyGluAsnGlyValGlnLysAspValSerGlnXaaSerIle Tyr|SerGlnThrGlu (SEQ.ID.NO.: 15), and d) GlyLysGlyIleSerSerGlnTyr|SerAsnThrGluGluArgLeu (SEQ.ID.NO.: 2);

wherein Xaa is any natural amino acid.

In an embodiment of the instant invention, the oligopeptides include oligomers that comprise an amino acid sequence that is selected from:

a) AsnLysIleSerTyrGln|SerSer (SEQ.ID.NO.: 16), b) AsnLysIleSerTyrGln|SerSerSer (SEQ.ID.NO.: 17), c) AlaAsnLysIleSerTyrGln|SerSerSer (SEQ.ID.NO.: 18), d) LysIleSerTyrGln|SerSerSerThrGlu (SEQ.ID.NO.: 19), e) GlyGluAsnGlyValGlnLysAspValSerGlnArgSerIle Tyr|SerGlnThrGlu (SEQ.ID.NO.: 4), and f) GlyGluAsnGlyValGlnLysAspValSerGlnSerSerIle Tyr|SerGlnThrGlu (SEQ.ID.NO.: 5).

In a more preferred embodiment of the instant invention, the oligopeptides include oligomers that comprise an amino acid sequence that is selected from:

a) AsnLysIleSerTyrGln|SerSerSerThr (SEQ.ID.NO.: 10), b) AsnLysIleSerTyrGln|SerSerSerThrGlu (SEQ.ID.NO.:3), c) AlaAsnLysIleSerTyrGln|SerSerSerThrGlu (SEQ.ID.NO.: 11), and d) GlyGluAsnGlyValGlnLysAspValSerGlnArgSerIle Tyr|SerGlnThrGlu (SEQ.ID.NO.: 4).

In a further embodiment of the instant invention, the oligopeptides include oligomers that comprise an amino acid sequence that is selected from:

a) GlyArgLysAlaAsnLysIleSerTyrGln|SerSerSerThr Glu GluArgArg LeuHisTyrGlyGluAsnGly (SEQ.ID.NO.: 6).

The phrase "oligomers that comprise an amino acid sequence" as used hereinabove, and elsewhere in the Detailed Description of the Invention, describes oligomers of from about 7 to about 100 amino acids residues which include in their amino acid sequence the specific amino acid sequence described and which are therefore proteolytically cleaved within the amino acid sequence described by free PSA. Thus, for example, the following oligomer:

GlnLeuAspAsnLysIleSerTyrGln|SerSerSerThrHis GlnSerSer (SEQ.ID.NO.: 20)

comprises the amino acid sequence:

AsnLysIleSerTyrGln|SerSerSerThr (SEQ.ID.NO.: 10)

and would therefore come within the instant invention. It is understood that such oligomers do not include semenogelin I and semenogelin II.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. The following list of amino acid replacements is meant to be illustrative and is not limiting:

| Original Amino Acid | Replacement Amino Acid(s) |
|---|---|
| Ala | Gly |
| Arg | Lys, ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg |
| Met | Leu, Ile, Nle, Val |
| Phe | Tyr, Trp |
| Ser | Thr |
| Thr | Ser |
| Trp | Phe, Tyr |
| Tyr | Phe, Trp |
| Val | Leu, Ile, Met, Nle |

Thus, for example, the following oligopeptides may be synthesized by techniques well known to persons of ordinary skill in the an and would be expected to be proteolytically cleaved by free PSA:

AsnArgIleSerTyrGln|Ser (SEQ.ID.NO.: 21)

AsnLysValSerTyrGln|Ser (SEQ.ID.NO.: 22)

AsnLysMetSerTyrGln|SerSer (SEQ.ID.NO.: 23)

AsnLysLeuSerTyrGln|SerSer (SEQ.ID.NO.: 24)

AsnLysIleThrTyrGln|SerSerSer (SEQ.ID.NO.: 25)

AsnLysIleSerPheGln|SerSerSer (SEQ.ID.NO.: 26)

AsnLysIleSerTrpGln|SerSerSerThr (SEQ.ID.NO.: 27)

AsnLysIleSerTyrAsn|SerSerSerThr (SEQ.ID.NO.: 28)

AsnLysIleSerTyrGln|ThrSerSerThr (SEQ.ID.NO.: 29)

AsnLysIleSerTyrGln|Ser (SEQ.ID.NO.: 30)

GlnLysIleSerTyrGln|SerSer (SEQ.ID.NO.: 31)

AsnArgIleThrTyrGln|SerSerSer (SEQ.ID.NO.: 32)

AsnArgIleSerPheGln|SerSerSerThr (SEQ.ID.NO.: 33)

AsnArgIleSerTrpGln|SerSerSerThr (SEQ.ID.NO.: 34)

AsnArgIleSerTyrGln|ThrSerSerThr (SEQ.ID.NO.: 35)

AsnLysIleThrTyrGln|ThrSerSerThr (SEQ.ID.NO.: 36)

AsnLysLeuSerTyrGln|ThrSerSerThr (SEQ.ID.NO.: 37)

GlnLysLeuSerTyrGln|SerSerSerThr (SEQ.ID.NO.: 38)

AsnArgLeuSerTyrGln|ThrSerSerThr (SEQ.ID.NO.: 39)

AsnLysValSerPheGln|SerSerSerThr (SEQ.ID.NO.: 40)

AsnArgValSerTrpGln|SerSerSerThr (SEQ.ID.NO.: 41)

GlnLysValSerTyrGln|SerSerSerThr (SEQ.ID.NO.: 42)

GlnLysIleSerTyrGln|ThrSerSerThr (SEQ.ID.NO.: 43)

AsnLysIleSerTyrGln|SerSerSerThr (SEQ.ID.NO.: 44)

Similarly, the following oligopeptides may be synthesized by techniques well known to persons of ordinary skill in the art and would be expected to be proteolytically cleaved by free PSA:

GlyGluGlnGlyValGlnLysAspValSerGlnSerSerIleTyr|SerGlnThrGlu (SEQ.ID.NO.: 45),

GlyGluAsnGlyLeuGlnLysAspValSerGlnSerSerIleTyr|SerGlnThrGlu (SEQ.ID.NO.: 46),

GlyGluAsnGlyValAsnLysAspValSerGlnSerSerIleTyr|SerGlnThrGlu (SEQ.ID.NO.: 47),

GlyGluAsnGlyValGlnArgAspValSerGlnArgSerIleTyr|SerGlnThrGlu (SEQ.ID.NO.: 48),

GlyGluAsnGlyValGlnLysAspValSerGlnLysSerIleTyr|SerGlnThrGlu (SEQ.ID.NO.: 49),

GlyGluAsnGlyValGlnLysAspLeuSerGlnThrSerIleTyr|SerGlnThrGlu (SEQ.ID.NO.: 50),

GlyGluAsnGlyValGlnLysAspValSerGlnSerSerIlePhe|SerGlnThrGlu (SEQ.ID.NO.: 51),

GlyGluAsnGlyValGlnLysAspMetSerGlnSerSerIleTyr|ThrGlnThrGlu (SEQ.ID.NO.: 52),

GlyGluAsnGlyValGlnLysAspValSerGlnArgSerIleTyr|ThrGlnThrGlu (SEQ.ID.NO.: 53),

GlyGluAsnGlyValGlnLysAspValSerGlnSerSerIleTyr|SerGlnSerGlu (SEQ.ID.NO.: 54), and GlyGluAsnGlyValGlnLysAspValSerGlnArgSerIleTyr|SerAsnThrGlu (SEQ.ID.NO.: 55);

GlyLysAlaIleSerSerGlnTyr|SerAsnThrGluGluArgLeu (SEQ.ID.NO.: 56),

GlyArgGlyIleSerSerGlnTyr|SerAsnThrGluGluArgLeu (SEQ.ID.NO.: 57),

GlyLysGlyIleThrSerGlnTyr|SerAsnThrGluGluArgLeu (SEQ.ID.NO.: 58),

GlyLysGlyIleSerThrGlnTyr|SerAsnThrGluGluArgLeu (SEQ.ID.NO.: 59),

GlyLysGlyIleSerSerAsnTyr|SerAsnThrGluGluArgLeu (SEQ.ID.NO.: 60),

AlaLysGlyIleSerSerGlnTyr|SerAsnThrGluGluArgLeu (SEQ.ID.NO.: 61),

GlyLysGlyIleSerSerGlnPhe|SerAsnThrGluGluArgLeu (SEQ.ID.NO.: 62),

GlyLysGlyIleSerSerGlnTyr|ThrAsnThrGluGluArgLeu (SEQ.ID.NO.: 63),

GlyLysGlyIleSerSerGlnTyr|SerAsnSerGluGluArgLeu (SEQ.ID.NO.: 64), and

GlyLysGlyIleSerSerGlnTyr|SerAsnThrAspGluArgLeu (SEQ.ID.NO.: 65); and the like.

The inclusion of the symbol "|" within an amino acid sequence indicates the point within that sequence where the oligopeptide is proteolytically cleaved by free PSA.

The invention also concerns a method for assaying proteolytic free PSA activity in a composition. This is an important aspect of the invention in that such an assay system provides one with the ability to measure quantitatively the amount of free PSA present in certain physiological fluids and tissues. Such an assay will also provide not only the ability to follow isolation and purification of free PSA, but also is a basis for a screening assay for inhibitors of the proteolytic activity of free PSA. The assay method generally includes simply determining the ability of a composition suspected of containing enzymatically active free PSA to proteolytically cleave the oligopeptide.

Typically, the assay protocol is carried out using one of the oligopeptides described hereinabove. However, one may find a particular benefit in construction of an assay wherein the oligopeptide containing the cleavage site is labeled so that one can measure the appearance of such a label, for example, a radioactive label, in both the uncleaved oligopeptide and the portion of the oligopeptide remaining after cleavage which contains the label.

The instant invention further relates to a method for identifying compounds (hereinafter referred to as candidate compounds) that will inhibit the proteolytic activity of free PSA. It is contemplated that this screening technique will prove useful in the general identification of any candidate compound that will serve such as an inhibitory purpose, whether or not the candidate compound is proteinaceous or peptidyl in structure.

Thus, the present invention is also directed to a method for determining the ability of a test substance to inhibit the proteolytic activity of free PSA, the method which comprises:

(a) reacting a substrate, wherein the substrate comprises a sequence of amino acids that is recognized and selectively proteolytically cleaved by free prostate specific antigen, with free prostate specific antigen in the presence of a test substance; and (b) detecting whether the substrate has been cleaved, in which the ability of the test substance to inhibit proteolytic activity of prostate specific antigen is indicated by a decrease in the cleavage of the substrate as compared to the cleavage of the substrate in the absence of the test substance.

The candidate screening assay is quite simple to set up and perform, and is related in many ways to the assay discussed above for determining proteolytic activity. Thus, after obtaining a relatively purified preparation of free PSA, one will desire to simply admix a test substance with the proteolytic preparation, preferably under conditions which would allow the PSA to perform its cleavage function but for inclusion of a inhibitory substance. Thus, for example, one will typically desire to include within the admixture an amount of a known oligopeptide having a PSA specific cleavage site, such as those oligopeptides described hereinabove. In this fashion, one can measure the ability of the test substance to reduce cleavage of the oligopeptide relatively in the presence of the test substance.

Accordingly, one will desire to measure or otherwise determine the activity of the free PSA in the absence of the added test substance relative to the activity in the presence of the test substance in order to assess the relative inhibitory capability of the test substance.

The instant invention also relates to novel anti-cancer compositions useful for the treatment of prostate cancer. Such compositions comprise the oligopeptides of the instant invention covalently bonded directly, or through a chemical linker, to a cytotoxic agent. Such a combination of an oligopeptide and cytotoxic agent may be termed a conjugate. Ideally, the cytotoxic activity of the cytotoxic agent is greatly reduced or absent when the oligopeptide containing the PSA proteolytic cleavage site is bonded directly, or through a chemical linker, to the cytotoxic agent and is intact. Also ideally, the cytotoxic activity of the cytotoxic agent increases significantly or returns to the activity of the unmodified cytotoxic agent upon proteolytic cleavage of the attached oligopeptide at the cleavage site. While it is not necessary for practicing this aspect of the invention, the most preferred embodiment of this aspect of the invention is a conjugate wherein the oligopeptide, and the chemical linker if present, are detached from the cytotoxic agent by the proteolytic activity of the free PSA and any other native x s proteolytic enzymes present in the tissue proximity, thereby releasing unmodified cytotoxic agent into the physiological environment at the place of proteolytic cleavage.

It is understood that the oligopeptide of the instant invention that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage.

Because the conjugates of the invention can be used for modifying a given biological response, cytotoxic agent is not to be construed as limited to classical chemical therapeutic agents. For example, the cytotoxic agent may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred cytotoxic agents include, in general, alkylating agents, antiproliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. One skilled in the art may make chemical modifications to the desired compound in order to make reactions of that compound more convenient for purposes of preparing conjugates of the invention.

A highly preferred group of cytotoxic agents for the present invention include drugs of the following formulae:

THE METHOTREXATE GROUP OF FORMULA (1):

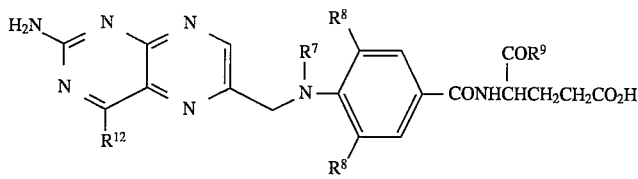

(1)

in which $R^{12}$ is amino or hydroxy;

$R^7$ is hydrogen or methyl;

$R^8$ is hydrogen, fluoro, chloro, bromo or iodo;

$R^9$ is hydroxy or a moiety which completes a salt of the carboxylic acid;

THE MITOMYCIN GROUP OF FORMULA (2):

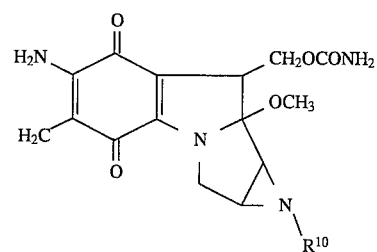

(2)

in which $R^{10}$ is hydrogen or methyl;

THE BLEOMYCIN GROUP OF FORMULA (3)

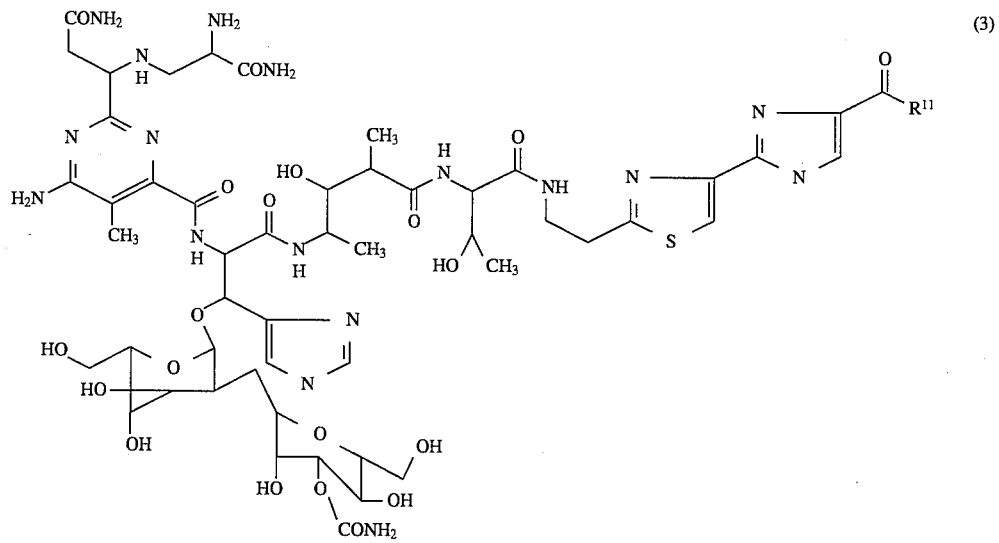

in which

R$^{11}$ is hydroxy, amino, C$_1$–C$_3$ alkylamino, di(C$_1$–C$_3$ alkyl)amino, C$_4$–C$_6$ polymethylene amino,

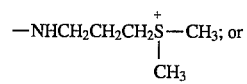

MELPHALAN OF FORMULA (4):

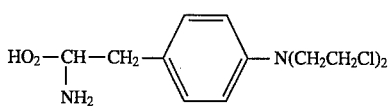

6-MERCAPTOPURINE OF FORMULA (5):

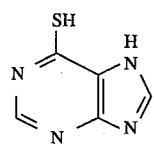

A CYTOSINE ARABINOSIDE OF FORMULA (6):

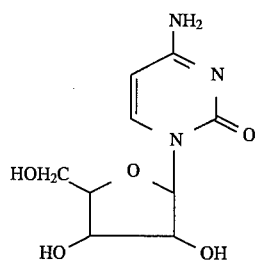

THE PODOPHYLLOTOXINS OF FORMULA (7):

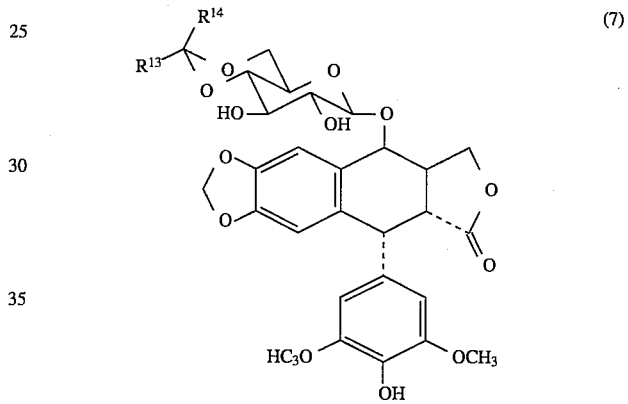

in which
  R$_{13}$ is hydrogen or methyl;
  R$_{14}$ is methyl or thienyl;
or a phosphate salt thereof;

THE VINCA ALKALOID GROUP OF DRUGS OF FORMULA (8):

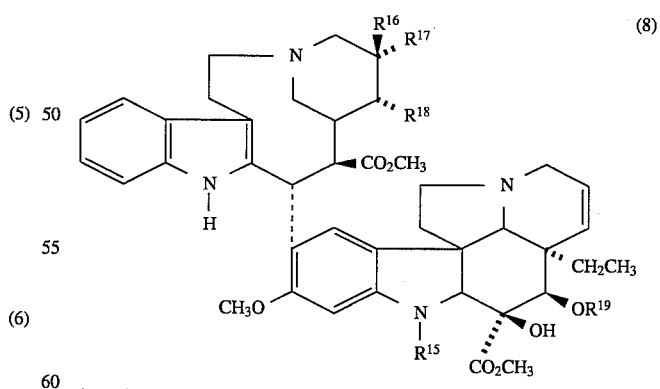

in which
  R$^{15}$ is H, CH$_3$ or CHO; when R$^{17}$ and R$^{18}$ are taken singly;
  R$^{18}$ is H, and one of R$^{16}$ and R$^{17}$ is ethyl and the other is H or OH; when R$^{17}$ and R$^{18}$ are taken together with the carbons to which they are attached, they form an oxirane ring in which case R$^{16}$ is ethyl;

$R^{19}$ is hydrogen, ($C_1$–$C_3$ alkyl)-CO, or chlorosubstituted ($C_1$–$C_3$ alkyl)-CO;

DIFLUORONUCLEOSIDES OF FORMULA (9):

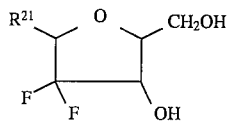   (9)

in which $R^{21}$ is a base of one of the formulae:

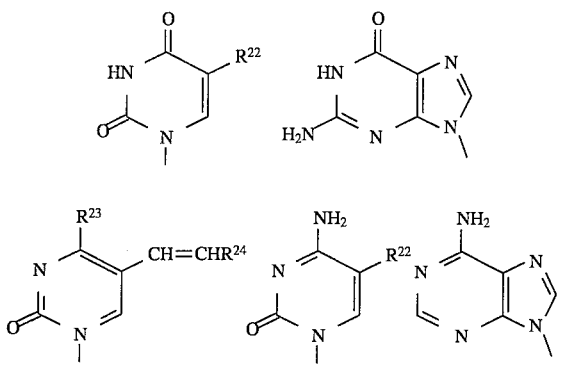

in which $R^{22}$ is hydrogen, methyl, bromo, fluoro, chloro or iodo;

$R^{23}$ is —OH or —$NH_2$;

$R^{24}$ is hydrogen, bromo, chloro or iodo; or,

THE ANTHRACYCLINES ANTIBIOTICS OF FORMULA (10):

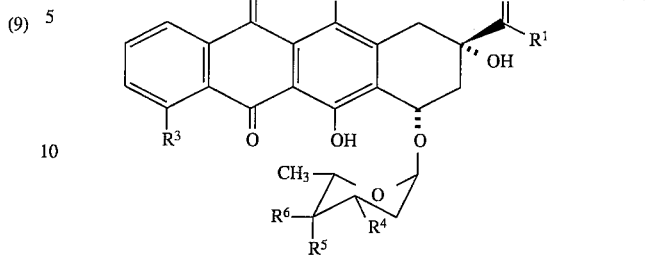   (10)

wherein $R^1$ is —$CH_3$, —$CH_2OH$, —$CH_2OCO(CH_2)_3CH_3$, or —$CH_2OCOCH\ (OC_2H_5)_2$;

$R_3$ is —$OCH_3$, —OH or —H;

$R_4$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine;

$R_5$ is —OH—OTHP or —H; and $R_6$ is —OH or —H provided that $R^6$ is not —OH when $R^5$ is —OH or —OTHP.

The most highly preferred drugs are the anthracycline antiobiotic agents of Formula (10), described previously. One skilled in the art understands that this structural formula includes compounds which are drugs, or are derivatives of drugs, which have acquired in the art different generic or trivial names. Table 1, which follows, represents a number of anthracycline drugs and their generic or trivial names and which are especially preferred for use in the present invention.

TABLE 1

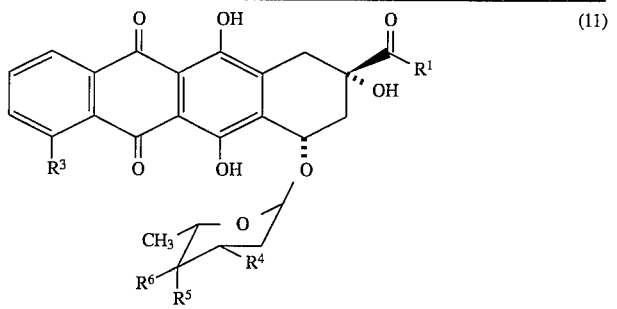   (11)

| Compound | $R_1$ | $R_3$ | $R_4$ | $R_5$ | $R_6$ |
|---|---|---|---|---|---|
| daunorubicin[a] | $CH_3$ | $OCH_3$ | $NH_2$ | OH | H |
| doxorubicin[b] | $CH_2OH$ | $OCH_3$ | $NH_2$ | OH | H |
| detorubicin | $CH_2OCOCH(OC_2H_5)_2$ | $OCH_3$ | $NH_2$ | OH | H |
| carminomycin | $CH_3$ | OH | $NH_2$ | OH | H |
| idarubicin | $CH_3$ | H | $NH_2$ | OH | H |
| epirubicin | $CH_2OH$ | $OCH_3$ | $NH_2$ | OH | OH |
| esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |

[a] "daunomycin" is an alternative name for daunorubicin
[b] "adriamycin" is an alternative name for doxorubicin Of the compounds shown in Table 1, the most highly preferred drug is doxorubicin. Doxorubicin (also referred to herein as "DOX") is that anthracycline of Formula (10) in which $R_1$ is —$CH_2OH$, $R_3$ is —$OCH_3$, $R_4$ is —$NH_2$, $R_5$ is —OH, and $R_6$ is —H.

The oligopeptides, peptide subunits and peptide derivatives (also termed "peptides") of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.)"Protective Groups in Organic Chemistry", Plenum Press, 1973; or Barony et al., "The Peptides: Analysis, Synthesis, Biology", 2, Chapter 1, Academic Press, 1980. The teachings of these works are hereby incorporated by reference.

The conjugates of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as a combination of 2-(1H-benzotriazol-1-yl)-1,3,3-tetramethyluronium hexafluorophosphate (known as HBTU) and 1-hydroxybenzotriazole hydrate (known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP) and the like may be utilized.

Furthermore, the instant conjugate may be formed by a non-peptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0] undec-7-ene.

The instant conjugate may also be formed by attachment of the oligopeptide to the cytotoxic agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond. Other such linker units which are stable to the physiological environment when not in the presence of free PSA, but are cleavable upon the cleavage of the PSA proteolytic cleavage site, are also envisioned. Furthermore, linker units may be utilized that, upon cleavage of the PSA proteolytic cleavage site, remain attached to the cytotoxic agent but do not significantly decrease the cytotoxic activity of such a post-cleavage cytotoxic agent derivative when compared with an unmodified cytotoxic agent.

One skilled in the art understands that in the synthesis of compounds of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, NY, N.Y. (1973); and, *Protective Groups in Organic Synthesis*, Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, β-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with the anthracycline antibiotic doxorubicin, the following Reaction Schemes illustrate the synthesis of the conjugates of the instant invention.

REACTION SCHEME I
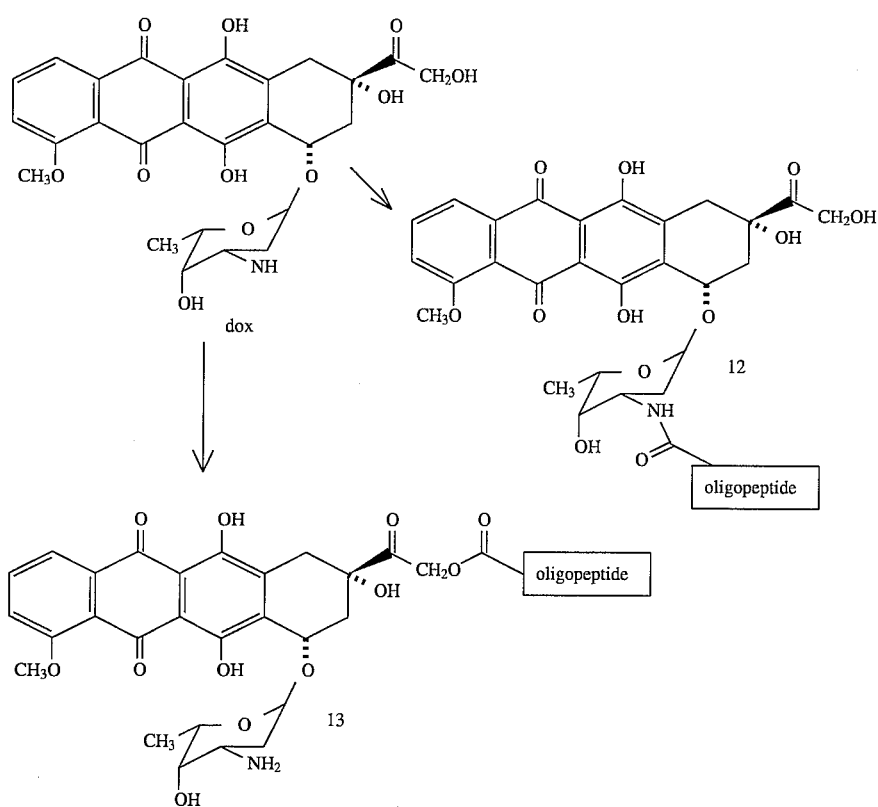
REACTION SCHEME II
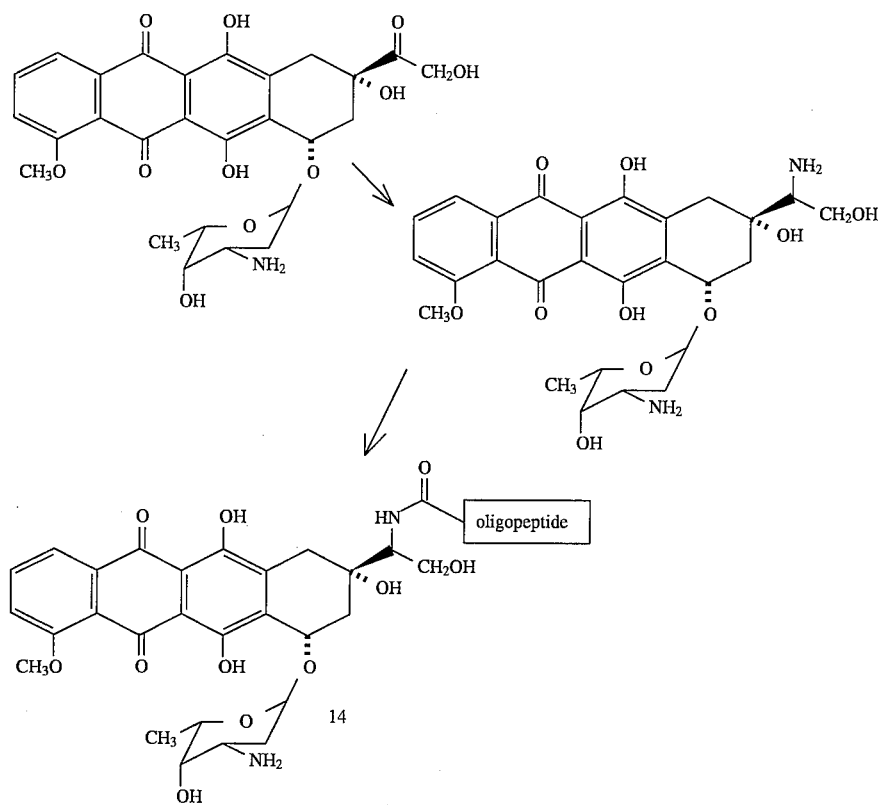

REACTION SCHEME III

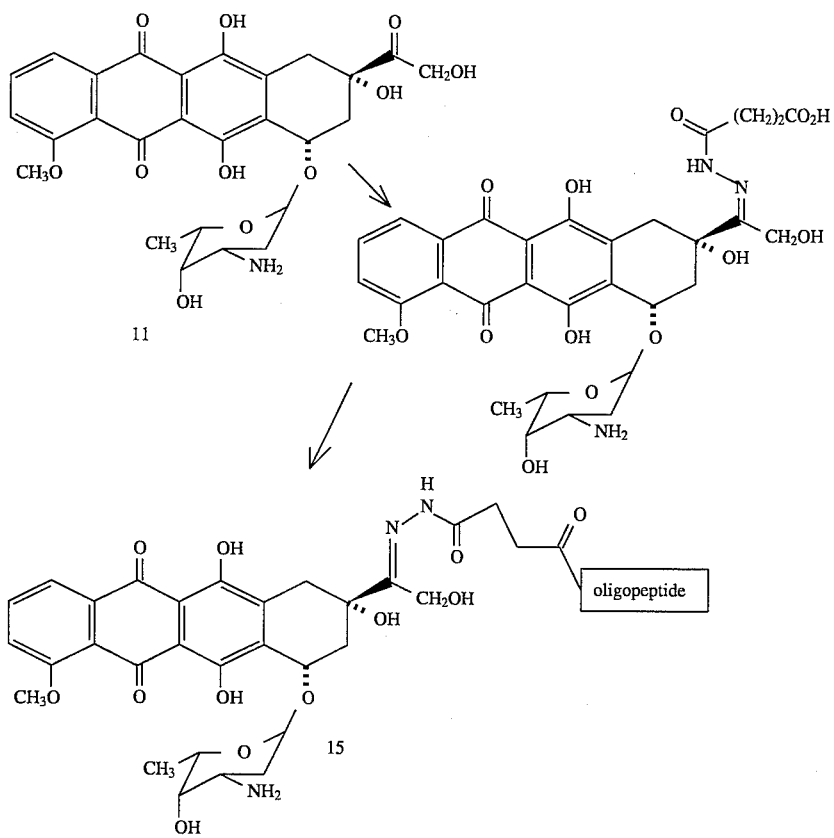

The following compounds are specific examples of the oligopeptide-cytotoxic agent conjugate of the instant invention:

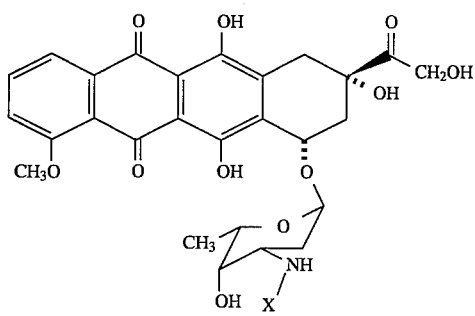

wherein
X is:

(SEQ. ID. NO.: 13)

(SEQ. ID. NO.: 16)

(SEQ. ID. NO.: 17)

(SEQ. ID. NO.: 10)

-continued

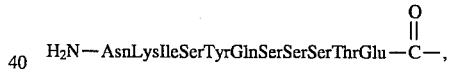
(SEQ. ID. NO.: 3)

or

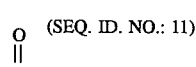
(SEQ. ID. NO.: 11)

The oligopeptide-cytotoxic agent conjugates of the invention are administered to the patient in the form of a pharmaceutical composition which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. *Remington's Pharmaceutical Sciences*, 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

EXAMPLE 1

Identification of the Semenogelin PSA Mediated Cleavage Site:

Liquefaction of the seminal gel parallels proteolytic fragmentation of semenogelin I [Lilja, H., Laurell, C. B., (1984) Scand. J. Clin. Lab. Inves. 44, 447–452]. It is believed that the proteolytic fragmentation of semenogelin is mainly due to the proteolytic activity of prostate-specific antigen [Lilja, H., (1985) J. Clin. Invest. 76, 1899–1903]. Utilizing the published sequence of semenogelin I [Lilja, H., Abrahamsson, P. A., Lundwall, A., (1989) J. of Biol. Chem. 264, 1894–1900] (FIG. 1 ) we designed polymerase chain reaction primers to clone the semenogelin cDNA from a commercially available prostatic cDNA library (Clonetech, Palo Alto, Calif.). The purified semenogelin cDNA was placed into the bacterial expression vector pTAC [Linemeyer, D. L., Kelly, L. J., Minke, J. G., Gimenez-Gallego, G., DeSalvo, J. and Thomas, K. A., (1987) Bio/Technology 5,960–965]. The semenogelin cDNA was designed so that a tubulin epitope was placed at the carboxyl end of semenogelin protein. The bacterially expressed semenogelin protein was purified on an anti-tubulin antibody column. The purified semenogelin I protein was mixed with commercially prepared prostate-specific antigen (PSA) (York Biologicals international, Stony Brook, N.Y.) in an 100 to 1 molar ratio (semenogelin I/PSA) in 12 mM Tris pH 8.0, 25 mM NaCl, 0.5 mM CaCl$_2$, and incubated for various times. The digest was fractionated by polyacrylamide gel electrophoresis and transferred by electrophoresis to ProBlott filter paper (Applied Biosystems, Inc., Foster City, Calif.) in CAPS buffer [Matsudaira, P., (1987) J. Biol. Chem. 252, 10035–10038]. The ProBlott filter paper was stained with coomassie blue to identify the novel PSA generated semenogelin I protein fragments. The novel fragments were cut out of the filter with a scalpel and submitted for sequence determination. After the proteolytic fragments were identified by variable time digestion, a 10 minute digestion reaction was performed. The affinity of PSA for the 5 potential cleavage sites in semenogelin I was determined to be as follows: site 349/350>site 375/376>site 289/290=site 315/316>site 159/160. The relative affinities were derived from the comassie blue staining intensity of each PSA generated peptide fragment. These intensities had approximate ratios of 3:1:0.6:0.3.

EXAMPLE 2

Preparation of Oligopeptides which Comprise the PSA Mediated Cleavage Site:

Oligopeptides were prepared by solid-phase synthesis, using a double coupling protocol for the introduction of amino acids on the Applied Biosystems model 430A automated peptide synthesizer. Deprotection and removal of the oligopeptide from the resin support were achieved by treatment with liquid hydrofluoric acid. The oligopeptides were purified by preparative high pressure liquid chromatography on reverse phase C18 silica columns using an aqueous 0.1% trifluoroacetic acid/acetonitrile gradient. Identity and homogeneity of the oligopeptides were confirmed by amino acid composition analysis, high pressure liquid chromatography, and fast atom bombardment mass spectral analysis. The following oligopeptides were prepared by this method:

SerTyrGln SerSerSerThrGlu (SEQ.ID.NO.: 7)

IleSerTyrGln SerSerSerThrGlu (SEQ.ID.NO.: 8)

LysIleSerTyrGln SerSerSerThrGlu (SEQ.ID.NO.: 9)

AsnLysIleSerTyrGln SerSerSerThrGlu (SEQ.ID.NO.: 3)

AsnLysIleSerTyrGln SerSerSerThr (SEQ.ID.NO.: 10)

AlaAsnLysIleSerTyrGln SerSerSerThrGlu (SEQ.ID.NO.: 11)

AlaAsnLysIleSerTyrGln SerSerSer (SEQ.ID.NO.: 18)

AsnLysIleSerTyrGln SerSerSer (SEQ.ID.NO.: 17)

GlyArgLysAlaAsnLysIleSerTyrGln SerSerSerThrGlu-GluArgArg LeuHisTyr GlyGluAsnGly (SEQ.ID.NO.: 6)

EXAMPLE 3

Assessment of the Recognition of Oligopeptides by Free PSA:

The oligopeptides prepared as described in Example 2 were individually dissolved in PSA digestion buffer (12 mM tris(hydroxymethyl)aminomethane pH8.0, 25 mM NaCl, 0.5 mM CaCl$_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1%TFA/acetonitrile gradient. The results of the assessment are shown in FIG. 2. The removal of an asparagine residue from the amino terminus of the oligopeptide results in a significant loss of PSA mediated peptide hydrolysis, while the presence of a glutamic acid residue at the carboxyl end of the peptide appears not to be essential to recognition by PSA.

EXAMPLE 4

Preparation of Non-cleavable Oligopeptide-Doxorubicin Conjugates:

The derivatives of doxorubicin shown in Table 3 were prepared using the following general reaction: To a mixture of doxorubicin (Sigma) and the corresponding peptide (prepared by solid phase synthesis or commercially available (Sigma)) in DMSO was added HBTU and HOBT along with diisopropylethylamine and the reaction mixture was stirred overnight. The crude reaction mixture was purified directly by preparative HPLC on a reversed-phase C-18 column using a 0.1% trifluoroacetic acid (TFA) in acetonitrile/0.1% TFA in water gradient.

TABLE 3

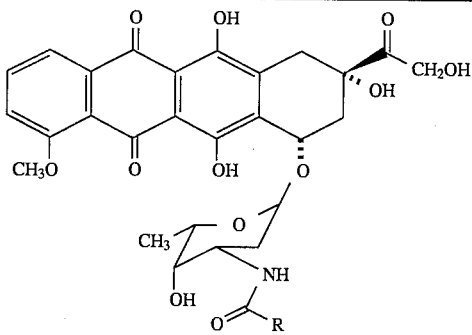

| Compound | R | MS (parent ion) |
|---|---|---|
| 12a | Ala—H | 615 |
| 12b | Ala—N—Ac | 657 |
| 12c | Ala—Ala—Ala—N—Ac | 799.5 |
| 12d | Ala—Ser—Ala—Gly—Thr—Pro—Gly—Ala—N—Ac (SEQ. ID. NO.: 12) | 1199 |

EXAMPLE 5

In vitro Assay of Cytotoxicity of Peptidyl Derivatives of Doxorubicin:

The cytotoxicities of the non-cleaveable oligopeptide-doxorubicin conjugates, prepared as described in Example 4, against a line of cells which is known to be killed by unmodified doxorubicin were assessed with an Alamar Blue assay. Specifically, cell cultures of LNCaP prostate tumor cells or Chinese hamster ovary cells transfected with pCMV-PSA in 96 well plates were diluted with medium containing various concentrations of a given conjugate (final plate well volume of 200 µl). The cells were incubated for 2 days at 37° C. and then 20 µl of Alamar Blue was added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of unmodified doxorubicin and unmodified oligopeptide were also assessed. FIG. 3 shows the cytotoxicity data for a representative compound (Compound 12d).

EXAMPLE 6

Assessment of Enzymatically Active PSA from LNCaP Cells

Enzymatic activity was demonstrated by incubating LNCaP serum free media (concentrated approximately 200 fold) with recombinant Senemogelin I protein. Approximately 0.5 µg of immunologically reactive PSA in concentrated conditioned media [determined by HYBRIDTECH (Tandem E) elisa] was mixed with approximately 3 µg of recombinant Semenogelin I and incubated for 4 hours at 37° C. At the end of the incubation, the digest mixture was analyzed by Western blot procedures. The results show that purified PSA from semen and PSA from LNCaP conditioned media generate identical proteolytic maps of the recombinant Semenogelin I protein. Thus, LNCap cells, which are a human metastatic prostate adenocarcinoma isolated from a needle biopsy of a lymph node (American Type Culture Collection, ATCC CRL 1740) produces enzymatically active PSA. LNCaP are tumorigenic in nude mice and produce detectable levels of circulating PSA.

EXAMPLE 7

Preparation of Cleavable Oligopeptide-Doxorubicin Conjugates:

The derivatives of doxorubicin wherein an oligopeptide which is proteolytically cleaved by free PSA is covalently attached to the amine of the sugar moiety of the doxorubicin are prepared using the following general reaction: To a mixture of doxorubicin (Sigma) and the corresponding peptide (prepared by solid phase synthesis or commercially available (Sigma)) in DMSO is added HBTU and HOBT along with diisopropylethylamine and the reaction mixture is stirred overnight. The crude reaction mixture is purified directly by preparative HPLC on a reversed-phase C-18 column using a 0.1% trifluoroacetic acid (TFA) in acetonitrile/0.1% TFA in water gradient.

EXAMPLE 8

In vitro Assay of Cytotoxicity of Peptidyl Derivatives of Doxorubicin:

The cytotoxicities of the cleaveable oligopeptide-Doxorubicin conjugates, prepared as described in Example 7, against a line of cells which is known to be killed by unmodified doxorubicin are assessed with an Alamar Blue assay as described in Example 5. Specifically, cell cultures of LNCap prostate tumor cells or Chinese hamster ovary cells transfected with pCMV-PSA in 96 well plates are diluted with medium containing various concentrations of a given conjugate (final plate well volume of 200 µl). The cells are incubated for 2 days at 37° C., 20 µl of Alamar Blue is added to the assay well. The cells are further incubated and the assay plates are read on a EL-310 ELISA reader at the dual wavelengths of 570 and 600 nm at 4 and 7 hours after addition of Alamar Blue. Relative percentage viability at the various concentration of conjugate tested is then calculated versus control (no conjugate) cultures. Cytotoxicities of the conjugates are also compared to the cytotoxicity of unmodified doxorubicin and unmodified oligopeptide assessed in the same assay.

What is claim is:

1. An oligopeptide that comprises a sequence of amino acids that is recognized and selectively proteolytically cleaved by free prostate specific antigen.

2. The oligopeptide according to claim 1 wherein the sequence of amino acids is
   a) AsnLysIleSerTyrGln|Ser (SEQ.ID.NO.: 13),
   b) LysIleSerTyrGln|Ser (SEQ.ID.NO.: 14),
   c) GlyGluAsnGlyValGlnLysAspValSerGlnXaaSerIle Tyr|SerGlnThrGlu (SEQ.ID.NO.: 15), or
   d) GlyLysGlyIleSerSerGlnTyr|SerAsnThrGluGluArgLeu (SEQ.ID.NO.: 2);
   wherein Xaa is any natural amino acid.

3. The oligopeptide according to claim 2 wherein the sequence of amino acids is
   a) AsnLysIleSerTyrGln|SerSer (SEQ.ID.NO.: 16),
   b) AsnLysIleSerTyrGln|SerSerSer (SEQ.ID.NO.: 17),
   c) AlaAsnLysIleSerTyrGln|SerSerSer (SEQ.ID.NO.: 18),
   d) LysIleSerTyrGln|SerSerSerThrGlu (SEQ.ID.NO.: 19),
   e) GlyGluAsnGlyValGlnLysAspValSerGlnArgSerIle Tyr|SerGlnThrGlu (SEQ.ID.NO.: 4), or
   f) GlyGluAsnGlyValGlnLysAspValSerGlnSerSerIle Tyr|SerGlnThrGlu (SEQ.ID.NO.: 5).

4. The oligopeptide according to claim 2 wherein the amino acid sequence is
   a) AsnLysIleSerTyrGln|SerSerSerThr (SEQ.ID.NO.: 10),
   b) AsnLysIleSerTyrGln|SerSerSerThrGlu (SEQ.ID.NO.: 3),
   c) AlaAsnLysIleSerTyrGln|SerSerSerThrGlu (SEQ.ID.NO.: 11), or
   d) GlyGluAsnGlyValGlnLysAspValSerGlnArgSerIle Tyr|SerGlnThrGlu (SEQ.ID.NO.: 4).

5. The oligopeptide according to claim 2 wherein the amino acid sequence is a) GlyArgLysAlaAsnLysIleSerTyrGln|SerSerSerThrGlu GluArgArg LeuHisTyrGlyGluAsnGly (SEQ.ID.NO.: 6).

6. The oligopeptide according to claim 1 which is selected from:
   AsnArgIleSerTyrGln|Ser (SEQ.ID.NO.: 21),
   AsnLysValSerTyrGln|Ser (SEQ.ID.NO.: 22),
   AsnLysMetSerTyrGln|SerSer (SEQ.ID.NO.: 23),
   AsnLysLeuSerTyrGln|SerSer (SEQ.ID.NO.: 24),
   AsnLysIleThrTyrGln|SerSerSer (SEQ.ID.NO.: 25),
   AsnLysIleSerPheGln|SerSerSer (SEQ.ID.NO.: 26),
   AsnLysIleSerTrpGln|SerSerSerThr (SEQ.ID.NO.: 27),
   AsnLysIleSerTyrAsn|SerSerSerThr (SEQ.ID.NO.: 28),
   AsnLysIleSerTyrGln|ThrSerSerThr (SEQ.ID.NO.: 29),
   AsnLysIleSerTyrGln|Ser (SEQ.ID.NO.: 30),
   GlnLysIleSerTyrGln|SerSer (SEQ.ID.NO.: 31),
   AsnArgIleThrTyrGln|SerSerSer (SEQ.ID.NO.: 32),
   AsnArgIleSerPheGln|SerSerSerThr (SEQ.ID.NO.: 33),
   AsnArgIleSerTrpGln|SerSerSerThr (SEQ.ID.NO.: 34),
   AsnArgIleSerTyrGln|ThrSerSerThr (SEQ.ID.NO.: 35),
   AsnLysIleThrTyrGln|ThrSerSerThr (SEQ.ID.NO.: 36),
   AsnLysLeuSerTyrGln|ThrSerSerThr (SEQ.ID.NO.: 37),
   GlnLysLeuSerTyrGln|SerSerSerThr (SEQ.ID.NO.: 38),
   AsnArgLeuSerTyrGln|ThrSerSerThr (SEQ.ID.NO.: 39),
   AsnLysValSerPheGln|SerSerSerThr (SEQ.ID.NO.: 40),
   AsnArgValSerTrpGln|SerSerSerThr (SEQ.ID.NO.: 41),
   GlnLysValSerTyrGln|SerSerSerThr (SEQ.ID.NO.: 42),
   GlnLysIleSerTyrGln|ThrSerSerThr (SEQ.ID.NO.: 43), or
   AsnLysIleSerTyrGln|SerSerSerThr (SEQ.ID.NO.: 44).

7. The oligopeptide according to claim 1 which is GlyGluGlnGlyValGlnLysAspValSerGlnSerSerIleTyr| SerGlnThrGlu (SEQ.ID.NO.: 45), GlyGluAsnGlyLeuGlnLysAspValSerGlnSerSerIleTyr|
SerGlnThrGlu (SEQ.ID.NO.: 46), GlyGluAsnGlyValAsnLysAspValSerGlnSerSerIle
TyrlSerGlnThrGlu (SEQ.ID.NO.: 47), GlyGluAsnGlyValGlnArgAspValSerGlnArgSerIle
TyrlSerGlnThrGlu (SEQ.ID.NO.: 48), GlyGluAsnGlyValGlnLysAspValSerGlnLysSerIle
TyrlSerGlnThrGlu (SEQ.ID.NO.: 49), GlyGluAsnGlyValGlnLysAspLeuSerGlnThrSerIle
TyrlSerGlnThrGlu (SEQ.ID.NO.: 50), GlyGluAsnGlyValGlnLysAspValSerGlnSerSerIle
Phe|SerGlnThrGlu (SEQ.ID.NO.: 51), GlyGluAsnGlyValGlnLysAspMetSerGlnSerSerIle
Tyr|ThrGlnThrGlu (SEQ.ID.NO.: 52), GlyGluAsnGlyValGlnLysAspValSerGlnArgSerIle
Tyr|ThrGlnThrGlu (SEQ.ID.NO.: 53), GlyGluAsnGlyValGlnLysAspValSerGlnSerSerIle
Tyr|SerGlnSerGlu (SEQ.ID.NO.: 54), GlyGluAsnGlyValGlnLysAspValSerGlnArgSerIle
Tyr|SerAsnThrGlu (SEQ.ID.NO.: 55);

GlyLysAlaIleSerSerGlnTyr|SerAsnThrGluGluArgLeu
(SEQ.ID.NO.: 56),

GlyArgGlyIleSerSerGlnTyr|SerAsnThrGluGluArgLeu
(SEQ.ID.NO.: 57),

GlyLysGlyIleThrSerGlnTyr|SerAsnThrGluGluArgLeu
(SEQ.ID.NO.: 58),

GlyLysGlyIleSerThrGlnTyr|SerAsnThrGluGluArgLeu
(SEQ.ID.NO.: 59),

GlyLysGlyIleSerSerAsnTyr|SerAsnThrGluGluArgLeu
(SEQ.ID.NO.: 60),

AlaLysGlyIleSerSerGlnTyr|SerAsnThrGluGluArgLeu
(SEQ.ID.NO.: 61),

GlyLysGlyIleSerSerGlnPhe|SerAsnThrGluGluArgLeu
(SEQ.ID.NO.: 62),

GlyLysGlyIleSerSerGlnTyr|ThrAsnThrGluGluArgLeu
(SEQ.ID.NO.: 63),

GlyLysGlyIleSerSerGlnTyr|SerAsnSerGluGluArgLeu
(SEQ.ID.NO.: 64), or

GlyLysGlyIleSerSerGlnTyr|SerAsnThrAspGluArgLeu
(SEQ.ID.NO.: 65).

8. An assay for determining proteolytic activity of free prostate specific antigen in a sample, comprising the steps of:

(a), reacting a substrate, wherein the substrate is an oligopeptide that comprises an oligomer of from about 7 to about 100 amino acids residues which includes in its amino acid sequence a specific sequence of amino acids that is recognized and selectively proteolytically cleaved by free prostate specific antigen, with the sample to give an assay mixture; and (b), detecting whether the substrate has been cleaved.

9. The assay according to claim 8 wherein the step of detecting whether the substrate has been cleaved comprises analyzing the assay mixture by high performance liquid chromatography.

10. The assay according to claim 8 wherein the oligopeptide comprises a sequence of amino acids that is selected from:

a) AsnLysIleSerTyrGln|Ser (SEQ.ID.NO.: 13), b) LysIleSerTyrGln|Ser (SEQ.ID.NO.: 14), c) GlyGluAsnGlyValGlnLysAspValSerGlnXaaSerIle
TyrlSerGlnThrGlu (SEQ.ID.NO.: 15), and d) GlyLysGlyIleSerSerGlnTyr|SerAsnThrGluGluArgLeu
(SEQ.ID.NO.: 2):

wherein Xaa is any natural amino acid.

11. The assay according to claim 8 wherein the assay further comprises the step (c):

(c), detecting the amount of the substrate that has been cleaved at various times, the times which are selected from 0.5 hour, 1 hour, 2 hours, 3 hours, 4 hours and 20 hours.

12. An assay for identifying compounds which inhibit the proteolytic activity of prostate specific antigen, comprising:

(a), reacting a substrate, wherein the substrate comprises a oligopeptide that comprises an oligomer of from about 7 to about 100 amino acids residues which includes in its amino acid sequence a specific sequence of amino acids that is recognized and selectively proteolytically cleaved by free prostate specific antigen, with free prostate specific antigen in the presence of a test substance to give an assay mixture; and (b), detecting whether the substrate has been cleaved, in which the ability of the test substance to inhibit proteolytic activity of prostate specific antigen is indicated by a decrease in the cleavage of the substrate as compared to the cleavage of the substrate in the absence of the test substance.

13. The assay according to claim 12 wherein the oligopeptide comprises a sequence of amino acids that is selected from:

a) AsnLysIleSerTyrGln|Ser (SEQ.ID.NO.: 13), b) LysIleSerTyrGln|Ser (SEQ.ID.NO.: 14), c) GlyGluAsnGlyValGlnLysAspValSerGlnXaaSerIle
TyrlSerGlnThrGlu (SEQ.ID.NO.: 15), and d) GlyLysGlyIleSerSerGlnTyr|SerAsnThrGluGluArgLeu
(SEQ.ID.NO.: 2);

wherein Xaa is any natural amino acid.

14. The assay according to claim 13 wherein the step of detecting whether the substrate has been cleaved comprises analyzing the assay mixture by high performance liquid chromatography.

15. The assay according to claim 8 wherein the detecting of the cleavage of the substrate in step (b) is performed at various times, the times which are selected from 0.5 hour, 1 hour, 2 hours, 3 hours, 4 hours and 20 hours.

* * * * *

UNITED STATES PATENT AND TRADEMARK OFFICE
CERTIFICATE OF CORRECTION

PATENT NO. : 5,599,686
DATED : June 28, 1994
INVENTOR(S) : Deborah DeFeo-Jones, Victor M. Garsky, Raymond E. Jones and Allen I. Oliff It is certified that error appears in the above-indentified patent and that said Letters Patent is hereby corrected as shown below:

In Column 61, line 40 should read as follows:

-- c) Gly GluAsnGlyValGlnLysAspValSerGlnXaaSerIle -- ; and

In Column 62, line 49 should read as follows:

--AsnArgIleThrTyrGlnIserSerSer (SEQ.ID.NO.: 32),--.

Signed and Sealed this

Fifteenth Day of July, 1997

Attest:

BRUCE LEHMAN

Attesting Officer

Commissioner of Patents and Trademarks